US00PP23873P2

(12) United States Plant Patent
Lintott et al.

(10) Patent No.: US PP23,873 P2
(45) Date of Patent: Sep. 3, 2013

(54) ***LEUCANTHEMUM* PLANT NAMED 'REAL GALAXY'**

(50) Latin Name: *Leucanthemum×superbum*
Varietal Denomination: REAL GALAXY

(76) Inventors: Keith Lintott, Bognor Regis (GB); Charles Richard Read, Bognor Regis (GB)

( * ) Notice: Subject to any disclaimer, the term of this patent is extended or adjusted under 35 U.S.C. 154(b) by 22 days.

(21) Appl. No.: 13/317,525

(22) Filed: Oct. 19, 2011

Related U.S. Application Data

(60) Provisional application No. 61/456,136, filed on Nov. 2, 2011.

(51) Int. Cl.
*A01H 5/00* (2006.01)

(52) U.S. Cl.
USPC ..... Plt./285

(58) Field of Classification Search
USPC ..... Plt./285
See application file for complete search history.

*Primary Examiner* — Susan McCormick Ewoldt

(57) ABSTRACT

A new cultivar of *Leucanthemum* plant named 'REAL GALAXY' that is distinguishable by tight clumping habit, mid-dark green foliage and formal inflorescences comprised of many white ray flowers surrounding a deep golden central disc and carried on strong stems. In combination these traits set 'REAL GALAXY' apart from all other existing varieties of *Leucanthemum* known to the inventor.

2 Drawing Sheets

Genus: *LEUCANTHEMUM.*
Species: ×*superbum.*
Denomination: 'REAL GALAXY'.

BACKGROUND OF THE INVENTION

The present invention relates to a new and distinct cultivar of *Leucanthemum* commonly known as Shasta daisy, which is grown as an ornamental plant for use in the garden and landscape. The new cultivar is known botanically as *Leucanthemum×superbum* and will be referred to hereinafter by the cultivar name 'REAL GALAXY'. *Leucanthemum* is a genus within the family Asteraceae in which the commonly referred to "flower" is botanically the inflorescence which is comprised of outer showy ray flowers surrounding smaller disc florets.

'REAL GALAXY' arose and was selected from an ongoing breeding program which is conducted by the inventors at the inventors' nursery in West Sussex, United Kingdom. The breeding program commenced in 2006 with the aim of developing new and improved commercial varieties of *Leucanthemum*. Each year's breeding cycle consists of controlled pollination between chosen male and female parents including unnamed and unreleased seedlings retained from previous breeding cycles. Seed from each year's cycle is harvested and sown in the fall, and new seedlings are raised and evaluated in the following summer.

'REAL GALAXY' is a seedling selection that resulted from the controlled pollination of a single plant of *Leucanthemum* 'Leukal 01' (U.S. Plant Pat. No. 15,204) as female parent, using pollen from a single plant of an unnamed and unreleased *Leucanthemum* seedling known to the inventors as 'L007' (unpatented) as male parent. The inventors selected 'REAL GALAXY' based on the criteria of vigor, formal flowers with many petals and strong stems. 'REAL GALAXY' is distinguishable from the female parent by the color of its ray flowers. Whereas 'Leukal 01' exhibits light cream-yellow ray flowers, the ray flowers of 'REAL GALAXY' are predominantly white with yellow "tips" (petal apices).

'REAL GALAXY' is distinguishable from the male parent by greater plant vigor and by greater number of ray flowers per inflorescence. In addition, the ray flowers of 'REAL GALAXY' are arranged in a more formal manner then either of its parents.

The variety of *Leucanthemum* which the inventor considers to be closest in flower form and plant habit to 'REAL GALAXY' is the female parent variety, 'Leukal 01' with which 'REAL GALAXY' is compared above. In addition, the inventor has observed that plants of 'REAL GALAXY' are typically later to come into bloom than plants of 'Leukal 01' grown under similar conditions. 'REAL GALAXY' blooms 10~12 days later than 'Leukal 01'. In addition to 'Leukal 01', 'REAL GALAXY' may be compared with other varieties of *Leucanthemum* which exhibit some degree of doubleness including *Leucanthemum* 'Engelina' (U.S. Plant Pat. No. 22,595) and *Leucanthemum* 'Aglaia' (not patented). Whereas the flowers of 'Engelina' and 'Aglaia' are fully double and almost globular, the flowers of 'REAL GALAXY' are distinctly formal in appearance being comprised of ray petals of mostly equal length and arranged in layers.

'REAL GALAXY' was first asexually propagated by the inventors in West Sussex, United Kingdom using the method of basal shoot cuttings. Since that time under careful observation 'REAL GALAXY' has been determined uniform, stable and true to type in subsequent generations of asexual propagation.

SUMMARY OF THE INVENTION

The following traits have been repeatedly observed and represent the distinguishing characteristics of 'REAL GALAXY'. In combination these traits set 'REAL GALAXY' apart from all other existing varieties of *Leucanthemum* known to the inventor. 'REAL GALAXY' has not been tested under all possible conditions and phenotypic differences may be observed with variations in environmental, climatic, and cultural conditions, however, without any variance in genotype.

1. 'REAL GALAXY' exhibits tight clumping habit.
2. The foliage of 'REAL GALAXY' is mid-dark green in color.
3. The inflorescence of 'REAL GALAXY' is 10 cm in diameter and comprised of ray flowers with many white petals arranged around a deep golden central disc.
4. The petals of the ray flowers are fine, fringed, and arranged in layers.
5. The inflorescence of 'REAL GALAXY' is carried on a strong stiff stem.
6. Flowering of 'REAL GALAXY' commences in early summer and continues until fall.
7. After one year of growth, plants of 'REAL GALAXY' are 65 cm in height and 60 cm in width.
8. 'REAL GALAXY' prefers a rich moist well-drained medium.
9. 'REAL GALAXY' is hardy in USDA Zone 5 (−20° F. or −28° C.).

BRIEF DESCRIPTION OF THE DRAWINGS

The accompanying color drawings illustrate the overall appearance of the new *Leucanthemum* cultivar named 'REAL GALAXY' showing the color of foliage and flower as true as is reasonably possible to obtain in color reproductions of this type. Color in the drawings may differ from color values cited in the detailed botanical description, which accurately describe the actual color of 'REAL GALAXY'.

Drawing labeled

Drawing labeled

Figure 1:
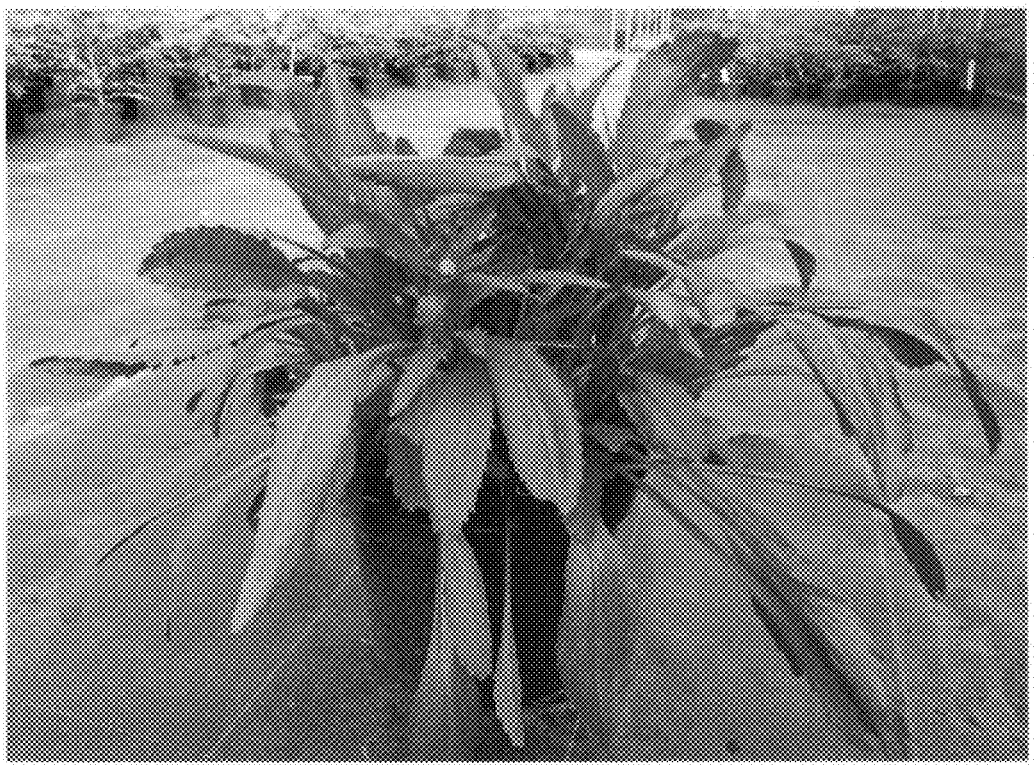
FIG. 1 illustrates in the foreground a 9-month-old plant of 'REAL GALAXY' growing in a 2-liter container at the inventors' nursery in West Sussex, United Kingdom.
Figure 2:
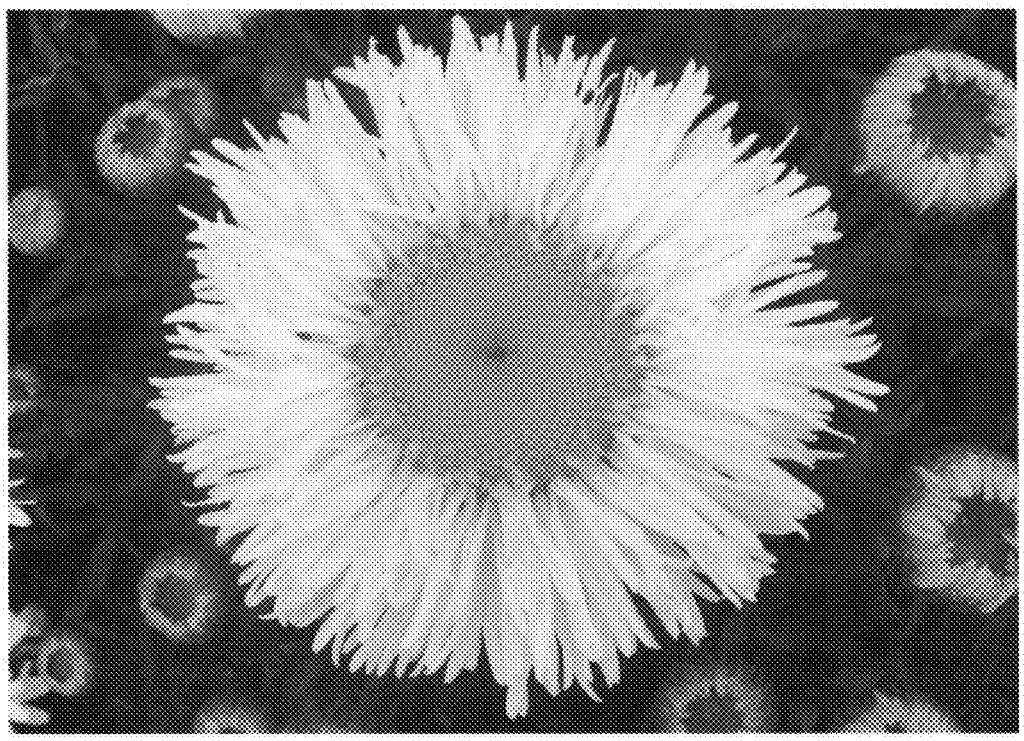
FIG. 2 depicts a close-up view of the flower on a 12-month-old plant of 'REAL GALAXY'.

Drawings were made using conventional techniques and although flower and foliage color may appear different from actual color due to light reflectance, it is as accurate as possible by conventional photography.

BOTANICAL DESCRIPTION OF THE PLANT

The following is a detailed botanical description of the new cultivar 'REAL GALAXY'. Observations, measurements, values and comparisons were collected in Arroyo Grande, Calif. during summer, from a 12-month-old plant growing out-of-doors in a 2-liter container. Color determinations are made in accordance with The 2001 Royal Horticultural Society Colour Chart from London, England, except where general color terms of ordinary dictionary significance are used.

Botanical classification: *Leucanthemum×superbum* 'REAL GALAXY'.

Family: Asteraceae (formerly Compositae).

Genus: *Leucanthemum.*

Species: ×*superbum.*

Denomination: 'REAL GALAXY'.

Common name: Shasta daisy.

Habit: Tight clumping habit.

Commercial category: Perennial herb.

Use: For garden and landscape.

Suggested commercial container size: 4-inch and 1-liter containers.

Parentage: *Leucanthemum×superbum* 'REAL GALAXY' is a seedling selection resulting from the deliberate controlled cross-pollination of the following parents:

*Female parent.*—An individual *Leucanthemum* 'Leukal 01' (U.S. Plant Pat. No. 15,204).

*Male parent.*—An unnamed individual *Leucanthemum* 'L007' (unpatented).

Propagation method: Basal shoot cuttings and division.

Rooting system: Fine and fibrous.

Vigor: Vigorous.

Time to develop roots (range): 14 to 20 days are needed for an initial cutting to develop roots.

Temperature to develop roots (range): The recommended air temperature is 20-21° Centigrade.

Crop time (range): 4-6 months to produce a 1-liter container from a basal shoot cutting.

Plant dimensions (first season): 65 cm in height and 60 cm in width.

Plant dimensions (at maturity): 65 cm in height and 60 cm in width.

Cultural requirements: Grow in full sun and rich, moist moderately fertile well-draining soil.

Pest or disease resistance: No disease or pest resistance known to the inventor.

Hardiness: USDA Zone 5.

Stem:

*Branching.*—Basal.
*Color.*—146A.
*Length* (*range*).—16 cm to 65 cm.
*Width* (*range*).—3 mm to 6 mm.
*Shape.*—Sub-cylindrical.
*Surface.*—Furrowed with sparse hairs.

Foliage:

*Type.*—Evergreen.
*Arrangement* (*combination*).—Opposite and basal.
*Internode length* (*range*).—3.50 to 7.50 cm.
*Division.*—Simple.
*Margin* (*range*).—Dentate to entire.
*Apex.*—Acute.
*Base.*—Attenuate.
*Leaf attachment* (*range*).—Basal to sub-sessile.
*Leaf color* (*abaxial surface*).—137B.
*Leaf color* (*adaxial surface*).—137A.
*Leaf shape.*—Lanceolate.
*Sub-sessile leaf length* (*average*).—7 cm.
*Sub-sessile leaf width* (*average*).—1 cm.
*Basal leaf length* (*average*).—20 cm.
*Basal leaf width* (*average*).—4 cm.
*Leaf venation.*—Pinnate.
*Vein color* (*abaxial and adaxial surfaces*).—137B.
*Leaf surface* (*abaxial*).—Glabrous.
*Leaf surface* (*adaxial*).—Glabrous.
*Fragrance.*—None observed.

Inflorescence:

*Inflorescence type.*—Capitula.
*Inflorescence quantity* (*average*).—25 buds and 5 flowers per 2-liter container plant.
*Inflorescence diameter.*—10 cm.
*Inflorescence depth.*—4 cm.
*Inflorescence arrangement.*—Terminal inflorescence.
*Inflorescence shape.*—Radiate.
*Inflorescence color.*—Central disc color (range): 17A-20A. Ray flower color: 155C.
*Fragrance.*—Sweet scent.
*Aspect.*—Facing upward.
*Bud dimensions.*—0.50 cm in length and 1 cm in diameter.
*Bud shape.*—Disc.
*Bud color.*—138A and 154B (range of 154B to 153B).
*Bud surface.*—Glabrous.

*Blooming season*.—Early summer to fall.

*Peduncle length* (*range*).—16 cm to 65 cm.

*Peduncle width* (*range*).—4 mm to 0.30 cm.

*Peduncle shape*.—Sub-cylindrical.

*Peduncle surface*.—Furrowed with sparse hairs.

*Peduncle color*.—146A.

*Ray flower*.—Ray flower shape (range): Tubular to trumpet shaped. Ray flower quantity (average): 50 per inflorescence. Ray flower color: 155C except petal apex ranging from 4A to 4B. Ray flower depth: 3 cm. Ray flower diameter (range): 1 cm to 1.50 cm. Ray flower corolla tube depth: 6 mm. Ray flower surface (abaxial): Glabrous. Ray flower surface (adaxial): Pubescent. Ray flower arrangement: Radiate. Petal quantity: 5 per ray flower. Petal shape: Fine strap-like. Petal appearance: Fringed. Petal surface (abaxial): Glabrous. Petal surface (adaxial): Pubescent. Petals fused or unfused: Basally fused. Petal apex: Rounded. Petal margin: Entire. Petal dimensions (average): 2.00 cm in length and 2 mm in width. Petal color (abaxial and adaxial surfaces): 155C except petal apex ranging from 4A to 4B.

*Involucral bract*.—Quantity (average): >25 per inflorescence. Bract color (abaxial and adaxial surfaces): 137B. Bract length (average): 8 mm. Bract width (average): 3 mm. Bract apex: Acute. Bract base (range): Rounded to truncate. Bract surface (abaxial and adaxial): Glabrous. Bract shape: Lanceolate. Bract margin: Entire.

*Disc floret*.—Disc floret quantity (average): >100 per inflorescence. Disc floret color: 20A. Disc floret dimensions: 7 mm in depth and <1 mm in diameter. Disc floret shape: Tubular. Petals: 5 in number. Fused or unfused: Fused. Petal apex: Acute. Self-cleaning or persistent: Self-cleaning. Receptacle color: 153B. Receptacle shape: Convex. Receptacle dimensions: 1 cm in height and 4 cm in diameter. Lastingness of inflorescence (range): 7-14 days.

*Reproductive organs*.—Stamen quantity: 2 in number. Stamen length: 1 mm. Stamen color: N155D. Pollen quantity: Moderate. Pollen color: 17A. Pistil quantity: 1 in number. Pistil length (range): 6 mm to 7 mm. Stigma height: 1 mm. Stigma width: <1 mm. Stigma form: Bifid. Stigma color: 151C. Ovary position: Superior. Ovary color: 151C. Ovary shape: Globose. Ovary dimensions: <1 mm in width and <1 mm in height.

*Seed*.—None observed to date.

The invention claimed is:

1. A new and distinct cultivar of *Leucanthemum* plant named 'REAL GALAXY' as described and illustrated herein.

* * * * *